United States Patent [19]

Banks et al.

[11] 4,329,385
[45] May 11, 1982

[54] TEXTURING POLYMER SURFACES BY TRANSFER CASTING

[75] Inventors: Bruce A. Banks, Olmsted Township, Cleveland County; Albert J. Weigand, Lakewood; James S. Sovey, Strongsville, all of Ohio

[73] Assignee: The United States of America as represented by the Administrator of the National Aeronautics and Space Administration, Washington, D.C.

[21] Appl. No.: 218,587

[22] Filed: Dec. 19, 1980

[51] Int. Cl.³ .................. B29D 7/02; C23C 15/00; B32B 27/16
[52] U.S. Cl. ..................... 428/141; 204/192 E; 204/192 EC; 264/22; 264/220
[58] Field of Search ............... 264/22, 220; 428/141; 204/192 E, 192 EC; 156/643

[56] References Cited

U.S. PATENT DOCUMENTS

| | | | |
|---|---|---|---|
| 2,876,187 | 3/1959 | Wolinski | 204/158 |
| 2,928,131 | 3/1960 | Mahler | 428/141 |
| 3,274,088 | 9/1966 | Wolinski | 204/165 |
| 3,752,731 | 8/1973 | Stiegler et al. | 161/164 |
| 3,761,338 | 9/1973 | Ungar et al. | 156/219 |
| 4,064,030 | 12/1977 | Nakai et al. | 204/192 |
| 4,114,983 | 9/1978 | Maffitt et al. | 350/164 |
| 4,199,650 | 4/1980 | Mirtich et al. | 428/421 |

*Primary Examiner*—Aaron Weisstuch
*Attorney, Agent, or Firm*—Gene E. Shook; John R. Manning; Norman T. Musial

[57] ABSTRACT

This invention is concerned with fabricating textured surfaces on polymers without altering their surface chemistries.

A surface of a fluorocarbon polymer 10 is exposed to a beam 12 of ions from a source 14 to texture it. The polymer 18 which is to be surface-roughened is then cast over the textured surface 20 of the fluorocarbon polymer. After curing, the cast polymer is peeled off the textured fluorocarbon polymer, and the peeled off surface 22 has a negative replica of the textured surface 20.

The microscopic surface texture provides large surface areas for adhesive bonding. In cardiovascular prosthesis applications the surfaces are relied on for the development of a thin adherent well nourished thrombus.

7 Claims, 3 Drawing Figures

TEXTURING POLYMER SURFACES BY TRANSFER CASTING

ORIGIN OF THE INVENTION

The invention described herein was made by employees of the United States Government and may be manufactured and used by or for the Government for governmental purposes without the payment of any royalties thereon or thereto.

TECHNICAL FIELD

This invention relates to a method of fabricating textured surfaces. The invention is particularly concerned with imparting a microscopic surface texture to polymers without altering their surface chemistries.

The microscopic surface texture on the polymer provides large surface areas for adhesive bonding and paint adhesion. In cardiovascular prosthesis applications the surfaces are relied on for the development of a thin, adherent, well nourished thrombus with the potential for reduced occurrence of thromboembolism.

BACKGROUND ART

A roughened base or master is coated with a strippable plastic material for transferring the surface roughness pattern to a plastic coating in prior art processes. Such methods are taught in Maffitt et al U.S. Pat. No. 4,114,983, Stiegler et al U.S. Pat. No. 3,752,731 and Mahler U.S. Pat. No. 2,928,131.

Radiation treatments of plastic films also have been suggested in the prior art. These treatments are relied on to enhance the adhesion properties of the material. Such treatments are disclosed in Nakai et al U.S. Pat. No. 4,064,030 and Wolinski U.S. Pat. No. 2,876,187 and 3,274,088. Other methods used to provide microscopically rough polymeric surfaces include salt particle dispersion casting and mechanical abrasion.

Certain disadvantages are inherent with these prior art methods. These disadvantages include an excessive thickness of the texture, inadequate uniformity of the texture, and the altering of the surface chemistries.

DISCLOSURE OF INVENTION

The method of the present invention utilizes ion beam sputtering for texturing the surface of a fluorocarbon polymer. The ion beam sputter textured surface is a microscopically rough texture resulting from spatial differences in sputter yield of the quasi crystalline fluorocarbon polymer. The textured surface also may be formed by sputter etching through a mesh or mask that produces an organized array of surface pits. Additionally, the textured surface may be formed by sputter etching through a disbursed fine particulate covering the fluropolymer.

The polymer to be surface roughened is cast over the textured surface of the flurocarbon polymer. The cast and cured polymer is then separated from the surface of the textured flurocarbon polymer.

BRIEF DESCRIPTION OF THE DRAWINGS

Details of the invention will be described in connection with the accompanying drawings wherein.

BEST MODE FOR CARRYING OUT THE INVENTION

Figure 1:
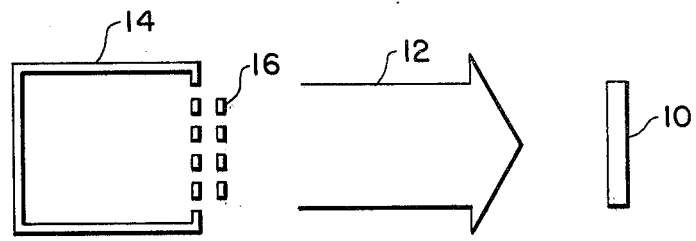
FIG. 1 is a schematic view of the ion beam texturing apparatus used to prepare the surfaces of the fluorocarbon polymers.

Referring now to the drawings, there is shown in FIG. 1 a fluorocarbon polymer 10 that is exposed to a beam 12 of ions in a manner described in U.S. Pat. No. 4,199,650. This beam 12 is preferably from an electron bombardment ion source 14 of the type developed from electric propulsion technology. Such an ion source is described in "Advances in Electronics and Electron Physics" by H. R. Kaufman, vol. 36, pages 365-373. Beam extraction is accomplished by a dished, two-grid ion optics system 16. Such a system is described in AIAA paper No. 76-1017 entitled "A 30 cm Diameter Argon Ion Source". Neutralization of the ion beam 12 can be achieved by secondary electrons released by ion bombardment of the vacuum facility walls or by use of a neutralizer.

The electron bombardment ion source 14 is located in a vacuum facility which is sufficiently large to minimize back sputtered facility material from contaminating the flurocarbon polymer. The vacuum facility is maintained at a pressure of about $4 \times 10^{-5}$ torr during the operation of the ion source.

The fluorocarbon polymer is positioned normal to the ion beam 12 at a location of about 20 centimeters from the ion source 14. The current density is between about 0.5 mA/cm$^2$ and 1.0 mA/cm$^2$. The beam 12 is uniform over the surface of the fluorocarbon polymer 10, and has an energy in the 200 eV to 2000 eV range. Among the fluorocarbon polymers that have been sputter-textured in this manner are polytetrafluoroethylene and fluoroethylene propylene. It is also contemplated that other fluorocarbon polymers can be used for ion beam texturing. Among these are polymers known commercially as PTFE Teflon, FEP Teflon, PFA Teflon, and Tefzel.

Figure 2:
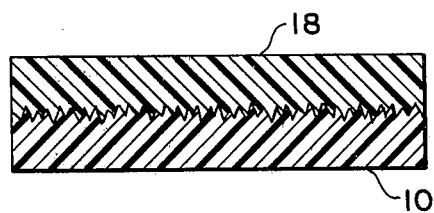
FIG. 2 is an enlarged sectional view showing a polymer cast over a textured fluorocarbon polymer.

As shown in FIG. 2 a polymer 18 which is to be surface-roughened is then cast over the textured fluorocarbon polymer 10 after the fluorocarbon polymer has been textured and removed from the vacuum facility. A wide variety of polymers can be cast over the textured fluorocarbon polymers.

Among the polymers which can be cast over the fluorocarbon polymers are silicone rubbers, polyurethanes, and polyolefins. It is further contemplated that other low elastic modulus polymers can be used as the casting polymers.

Figure 3:
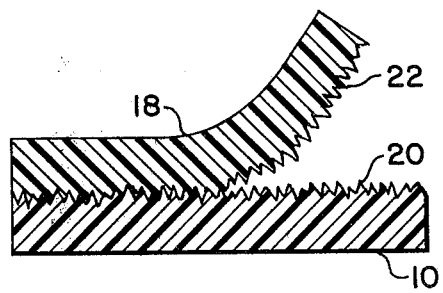
FIG. 3 is an enlarged sectional view similar to FIG. 2 showing the surface roughened polymer being stripped from the textured fluorocarbon polymer.

The cast and cured polymer 18 is then peeled off the textured fluorocarbon polymer 10 as shown in FIG. 3. The non-stick fluoropolymer surfaces 20 aid in the removal of the cast polymer 18 and its separation from the fluorocarbon polymer. The peeled off surface 22 of the cast polymer then has a negative replica of the textured fluorocarbon polymer surface 20.

While a preferred embodiment of the invention has been described, it is contemplated that various modifications may be made without departing from the spirit of the invention or the scope of the subjoined claims. By way of example, various inorganic, organic, non-metallic and metallic ion beam textured substrates can be used for the negative casting by sputtering a thin fluorocarbon polymer coating over the texture to allow release of the cast polymer.

We claim:

1. A method for texturing the surfaces of a polymer without altering the chemistry of the same comprising the steps of placing a fluorocarbon polymer in a vacuum environment of about $4 \times 10^{-5}$ torr, exposing at least one surface of said fluorocarbon polymer to a neutralized beam of ions having an energy between about 200 eV and 2000 eV and an ion beam current density between 0.5 mA/cm$^2$ and 1.0 mA/cm$^2$ to texture the same, removing said fluorocarbon polymer from said vacuum environment, casting a polymer over said textured surface of said fluorocarbon polymer and curing the same, and separating said cast and cured polymer from said fluorocarbon polymer whereby the surface of said polymer has a negative replica of said textured surface of said fluorocarbon polymer.

2. A method of texturing the surface of a polymer as claimed in claim 1 including providing a source of argon ions in said vacuum environment, and positioning said fluorocarbon polymer in the beam of argon ions at a location of about 20 centimeters from said source, said at least one surface being substantially normal to said beam.

3. A method of texturing the surface of a polymer as claimed in claim 2 wherein the argon ion beam is substantially uniform over said at least one surface.

4. A method of texturing the surface of a polymer as claimed in claim 1 wherein the fluorocarbon polymer is first sputtered onto a substrate.

5. A method of texturing the surface of a polymer as claimed in claim 1 wherein said polymer is selected from the group consisting of silicone rubbers, polyurethanes, and polyolefins.

6. A method of texturing the surface of a polymer as claimed in claim 1 including the step of applying a release agent to said textured surface prior to casting said polymer over the same.

7. A polymer article textured according to the process of claim 1.

* * * * *